(12) United States Patent
Butcher et al.

(10) Patent No.: US 10,820,825 B2
(45) Date of Patent: Nov. 3, 2020

(54) METHOD AND DEVICE FOR EVALUATION OF LOCAL TISSUE'S BIOLOGICAL OR BIOMECHANICAL CHARACTER

(75) Inventors: Jonathan Butcher, Ithaca, NY (US); Russell Gould, Yardley, PA (US)

(73) Assignee: Cornell University, Ithaca, NY (US)

( * ) Notice: Subject to any disclaimer, the term of this patent is extended or adjusted under 35 U.S.C. 154(b) by 1144 days.

(21) Appl. No.: 13/125,421

(22) PCT Filed: Oct. 22, 2009

(86) PCT No.: PCT/US2009/061680
§ 371 (c)(1),
(2), (4) Date: Jul. 11, 2011

(87) PCT Pub. No.: WO2010/048402
PCT Pub. Date: Apr. 29, 2010

(65) Prior Publication Data
US 2013/0190597 A1     Jul. 25, 2013

Related U.S. Application Data

(60) Provisional application No. 61/107,551, filed on Oct. 22, 2008.

(51) Int. Cl.
*A61B 5/05*      (2006.01)
*A61B 5/053*      (2006.01)

(52) U.S. Cl.
CPC .............. *A61B 5/05* (2013.01); *A61B 5/0536* (2013.01)

(58) Field of Classification Search
CPC ................................ A61B 5/05; A61B 5/0536
(Continued)

(56) References Cited

U.S. PATENT DOCUMENTS 3,604,958 A * 9/1971 Palini ............................ 310/319
4,116,198 A * 9/1978 Roos ............................... 606/46
(Continued)

FOREIGN PATENT DOCUMENTS

EP      0 807 407 B1     11/2002
WO    WO-99/52430       10/1999
(Continued)

OTHER PUBLICATIONS

International Search Report and Written Opinion for related International Application No. PCT/US2009/061680; report dated Jun. 3, 2010.
(Continued)

*Primary Examiner* — Boniface N Nganga
(74) *Attorney, Agent, or Firm* — Troutman Pepper Hamilton Sanders LLP (Rochester)

(57) ABSTRACT

A device for evaluation of a tissue's biological or biomechanical character is disclosed. The device uses negative pressure to draw a portion of the tissue across one or more electrode pairs disposed within the device. By measuring one or more parameters associated with an electric or magnetic field defined by the electrode pairs, in vivo evaluation of the tissue's biological or biomechanical character may be achieved in a minimally invasive manner. The device may also include an indenter to apply a positive stress on the tissue within the sidewall to further evaluate its biological or biomechanical character. A method of using the device is also disclosed.

25 Claims, 7 Drawing Sheets

(58) Field of Classification Search
USPC .................................. 600/407–480; 601/2–4
See application file for complete search history.

(56) References Cited

U.S. PATENT DOCUMENTS

| | | | |
|---|---|---|---|
| 4,754,763 A | 7/1988 | Doemland | |
| 5,213,110 A | 5/1993 | Kedem et al. | |
| 5,278,776 A * | 1/1994 | Fisher | A61B 5/0055 600/587 |
| 5,735,280 A * | 4/1998 | Sherman et al. | 600/1 |
| 5,791,337 A * | 8/1998 | Coles et al. | 128/200.26 |
| 5,810,806 A | 9/1998 | Ritchart et al. | |
| 5,913,857 A | 6/1999 | Ritchart et al. | |
| 6,022,362 A | 2/2000 | Lee et al. | |
| 6,270,464 B1 | 8/2001 | Fulton, III et al. | |
| 6,273,862 B1 | 8/2001 | Privitera et al. | |
| 6,423,081 B1 | 7/2002 | Lee et al. | |
| 6,432,064 B1 | 8/2002 | Hibner et al. | |
| 6,485,436 B1 | 11/2002 | Truckai et al. | |
| 6,723,049 B2 | 4/2004 | Skladnev et al. | |
| 6,738,674 B2 * | 5/2004 | Osypka | 607/122 |
| 6,743,228 B2 | 6/2004 | Lee et al. | |
| 6,813,515 B2 * | 11/2004 | Hashimshony | A61B 5/0507 324/632 |
| 6,969,358 B2 | 11/2005 | Baltschun et al. | |
| 7,416,550 B2 * | 8/2008 | Protsenko | A61B 18/14 606/32 |
| 7,435,232 B2 | 10/2008 | Liebschner | |
| 7,591,790 B2 | 9/2009 | Pflueger | |
| 8,062,465 B1 * | 11/2011 | Huang et al. | 156/308.2 |
| 8,116,845 B2 * | 2/2012 | Hashimshony et al. | 600/421 |
| 2002/0058882 A1 | 5/2002 | Fulton, III et al. | |
| 2003/0088245 A1 * | 5/2003 | Woloszko et al. | 606/41 |
| 2003/0171664 A1 | 9/2003 | Wendlandt | |
| 2003/0216663 A1 * | 11/2003 | Jersey-Willuhn | A61B 5/0536 600/547 |
| 2004/0034280 A1 | 2/2004 | Privitera et al. | |
| 2005/0119545 A1 | 6/2005 | Swanson | |
| 2005/0203440 A1 | 9/2005 | Gellman et al. | |
| 2007/0032739 A1 | 2/2007 | Hashimshony et al. | |
| 2008/0045859 A1 | 2/2008 | Fritsch et al. | |
| 2008/0167585 A1 * | 7/2008 | Khen | A61B 18/14 601/6 |
| 2009/0198149 A1 | 8/2009 | Privitera et al. | |

FOREIGN PATENT DOCUMENTS

| | | |
|---|---|---|
| WO | WO-2005/086724 A1 | 9/2005 |
| WO | WO-2008/119992 A2 | 10/2008 |

OTHER PUBLICATIONS

International Preliminary Report on Patentability for related International Application No. PCT/US2009/061680; report dated May 5, 2011.

* cited by examiner

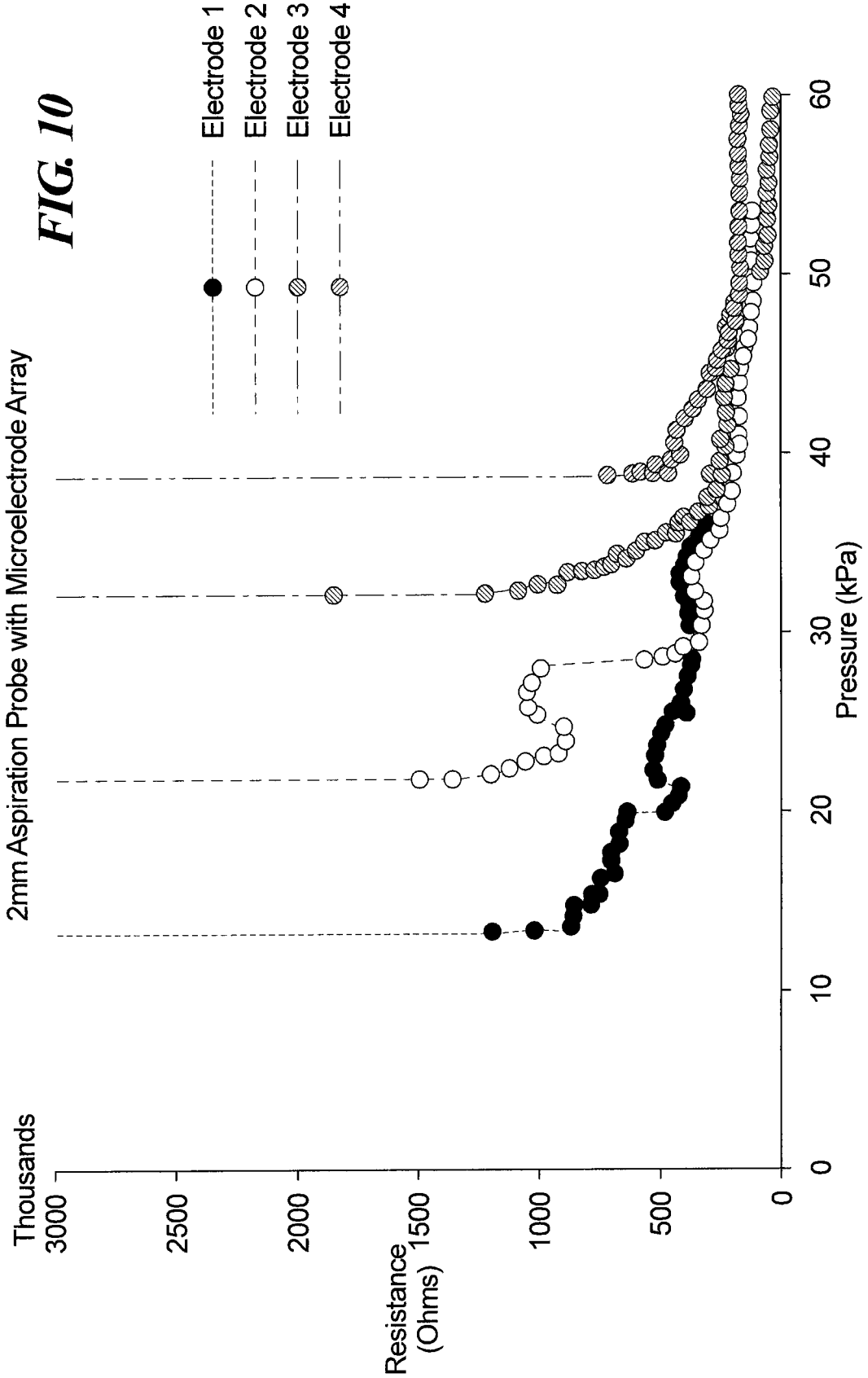

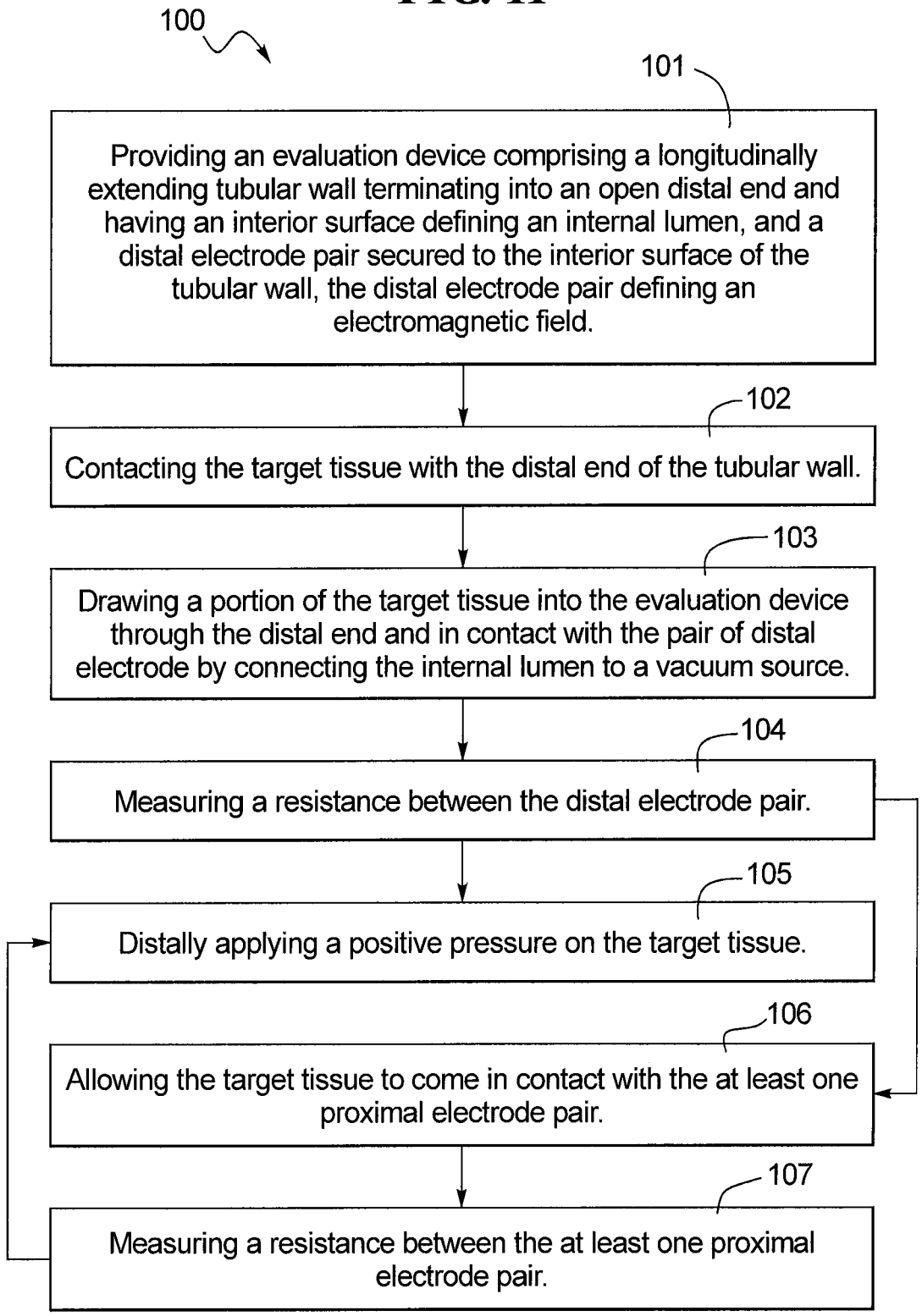

ion of PCT/US09/61680 filed on Oct. 22, 2009 and claims priority under 35 USC 119(e) to U.S. Provisional Patent Application No. 61/107,551 filed on Oct. 22, 2008.

METHOD AND DEVICE FOR EVALUATION OF LOCAL TISSUE'S BIOLOGICAL OR BIOMECHANICAL CHARACTER

CROSS-REFERENCE TO RELATED APPLICATION

This application is a U.S. National Stage Patent Application of PCT/US09/61680 filed on Oct. 22, 2009 and claims priority under 35 USC 119(e) to U.S. Provisional Patent Application No. 61/107,551 filed on Oct. 22, 2008.

BACKGROUND

1. Technical Field

A device for evaluation of a tissue's biological or biomechanical character is disclosed. The device uses negative pressure to draw a portion of the tissue across one or more electrode pairs disposed within the device. By measuring one or more parameters associated with an electric or magnetic field defined by the electrode pairs, in vivo evaluation of the tissue's biological or biomechanical character may be achieved in a minimally invasive manner. The device may also include an indenter to apply a positive stress on the tissue within the sidewall to further evaluate its biological or biomechanical character. A method of using the device is also disclosed.

2. Description of the Related Art

Evaluation of a tissue's biological or biomechanical character is becoming more and more important for a wide variety of medical applications. For example, recent studies have suggested that matrix tension and rigidity may play strong roles in oncogenic transformation and tissue fibrosis. The mechanical properties of biological tissue are diverse and complex because of the non-linear and elastic behaviors of tissues, which typically have layers of different proteins, organic substances, and fluids making the properties inhomogeneous. Because normal and diseased states of tissues often exhibit different biological and biomechanical characters, measurement of such properties may be used to detect tissue abnormalities that are characteristic of various medical conditions, such as cancer. Additionally, differences in biological states in soft tissues are revealed at different levels of applied mechanical stress. Currently, measurements of a tissue biomechanical character are generally accomplished in vitro by testing on tissues removed through biopsy.

As a minimally invasive alternative to biopsy, pipette aspiration has been recently used as a method to evaluate and measure the biomechanical properties of a tissue sample, and the information can be used as a parameter in classifying the tissue's state of health. In pipette aspiration, a portion of a tissue sample is drawn into a pipette under negative pressure. Specifically, the tissue distends into the tip of the pipette, and the height of elongation can be recorded optically, such as through optical instruments or visual observation (if the pipette is graduated). The elongation of tissue and the negative pressure applied are combined into a stress-strain curve to evaluate the biomechanics of the tissue under test. Alternatively, the data could be fit to empirical relationships that were based on prior testing of tissues with established health states for diagnostic purposes. After the test is finished, the negative pressure is removed and the tissue sample is restored to its original, non-deformed condition without tearing or ripping.

Although a device combining an aspiration tube and an optical recorder may be useful as a minimally invasive alternative to biopsy, the device usually requires relatively complicated equipments such as mirrors and an array of cameras positioned near the tip of the aspiration tube to obtain precise deformation data of the tissue within the tube. Thus, such a device may not be suitable for in vivo tissue biomechanical evaluations as the distal end profile of the device makes it difficult to reach the tissue site.

Use of an electrode pair or an array of electrode pairs to evaluate bone tissues has been reported in a limited number of academic studies. For example, a rudimentary "image" based on electric resistance can be generated by attaching an array of electrodes to the tested bone tissue. In some instances, correlation between the electric resistance "image" and the composition of the bone tissues may be established. However, existing methods based on electrode array merely evaluate tissues in their natural static state, and therefore may not be sufficient to provide a dynamic and responsive evaluation of tissue biomechanics for diagnostic purposes.

Finally, tissue evaluation by using an indenter has been reported to predict a tissue's biomechanical properties. Specifically, the indenter may include a mechanical probe, for applying a positive stress on the tissue to be tested. The indenter is connected to one or more sensors, such as pressure sensors and/or position sensors, to measure the reaction of the tested tissue toward the positive stress applied thereon. Nevertheless, one problem associated with the indenter systems is that the evaluation would require the test tissue to be secured or immobilized in order to obtain meaningful and reliable data, which may be difficult under in vivo conditions.

Hence, there is a need for a device for minimally invasive and in vivo evaluation of a tissue's biological or biomechanical character. Moreover, there is a need for a low profile tissue evaluation device that is reliable and easy to operate. Finally, there is a need for a tissue evaluation device that combines more than one evaluation techniques to further improve differentiation of tissue's biological states.

SUMMARY OF THE DISCLOSURE

In satisfaction of the aforementioned needs, a device for evaluation of a tissue's biological or biomechanical character is disclosed. In a general embodiment, the disclosed device may include a longitudinally extending sidewall, the sidewall having an interior surface defining an internal lumen adapted to be operatively connected to a vacuum source; a distal electrode pair disposed within the internal lumen, the electrode pair defining an electric or magnetic field; and a detector operatively connected to the distal electrode pair to detect at least one parameter associated with the electric or magnetic field. The device may also include an optional indenter adapted to apply a positive stress on the tissue within the internal lumen. The distal electrode pair may be secured to the interior surface of the sidewall, the optional indenter, or a combination of both.

In one embodiment of the disclosed device, the distal electrode pair includes two electrodes positioned directly opposite to each other. The electrodes may be made from a sheet metal material and may be adhesively secured to the interior surface of the sidewall. The distal electrode pair may be connected to the detector through a pair of insulated wires or wirelessly so as to allow the detector to measure one or more parameters of the electric or magnetic field, such as the resistance between the distal electrode pair.

In a further embodiment, the disclosed device may further include at least one proximal electrode pair disposed within the internal lumen and proximal to the distal electrode pair.

The at least one proximal electrode pair may be secured to the interior surface of the sidewall, the optional indenter, or a combination of both. Moreover, the at least one proximal electrode pair may be operatively connected to the detector, such as through one or more insulated wires so as to allow the detector to simultaneously measure one or more parameters associated with the electric or magnetic fields defined by the proximal and distal electrode pairs. The proximal and distal electrode pairs may be connected to the detector through a multi-pin micro-connector or wirelessly.

Similar to the distal electrode pair, each proximal electrode pair may include two electrodes positioned directly opposite to each other. Moreover, the proximal and distal electrode pairs may be arranged to form a longitudinally in-line array of electrode pairs.

To further improve the performance of the evaluation device, the device may include an optional indenter adapted to apply a positive stress on the tested tissue and evaluate its response to such a pressure. For example, the indenter may include a probe adapted to move in a distal direction within the internal lumen. The probe may be connected to a sensor that measures the position of the probe, the force or pressure exerted on the tested tissue by the probe, or other suitable parameters. Moreover, the measurements obtained by the indenter can be combined with the one or more parameters associated with the electric or magnetic field to further enhance the evaluation performance of the disclosed device.

In another aspect of this disclosure, a method for evaluating biological or biomechanical character of a target tissue is disclosed. The method may include the steps of providing a evaluation device comprising a longitudinally extending sidewall terminating into an open distal end and having an interior surface defining an internal lumen, and a distal electrode pair secured to the interior surface of the sidewall, the electrode pair defining an electric or magnetic field; contacting the target tissue with the distal end of the sidewall; drawing a portion of the target tissue into the evaluation device through the distal end and in contact with the distal electrode pair by connecting the internal lumen to a vacuum source; and measuring one or more parameters associated with the electric or magnetic field, such as the resistance between the distal electrode pair. In a refinement, the method may further include the step of applying a positive stress on the target tissue within the internal lumen.

In another embodiment in which the evaluation device may further include at least one proximal electrode pair operatively connected to the detector and secured to the interior surface of sidewall proximal to the distal electrode pair, the method may further include the optional step of allowing the target tissue to come in contact with the at least one proximal electrode pair and measuring one or more parameters associated with the electric or magnetic field defined by the proximal electrode pair, such as the resistance between the proximal electrode pair.

Other advantages and features of the disclosed methods and device will be described in greater detail below. It will also be noted here and elsewhere that the device or method disclosed herein may be suitably modified to be used in a wide variety of applications by one of ordinary skill in the art without undue experimentation.

BRIEF DESCRIPTION OF THE DRAWINGS

For a more complete understanding of the disclosed device and method, reference should be made to the embodiments illustrated in greater detail in the accompanying drawings, wherein:

FIG. 10 is graphic illustration of the relationship between the resistance and the negative pressure applied to the tested tissue in the embodiment shown in FIGS. 6-9;

FIG. 11 is a schematic block diagram of a method of evaluating tissue biomechanics according to another aspect of this disclosure;

It should be understood that the drawings are not necessarily to scale and that the disclosed embodiments are sometimes illustrated diagrammatically and in partial views. In certain instances, details which are not necessary for an understanding of the disclosed device or method which render other details difficult to perceive may have been omitted. It should be understood, of course, that this disclosure is not limited to the particular embodiments illustrated herein.

DETAILED DESCRIPTION OF THE DISCLOSURE

Figure 1:
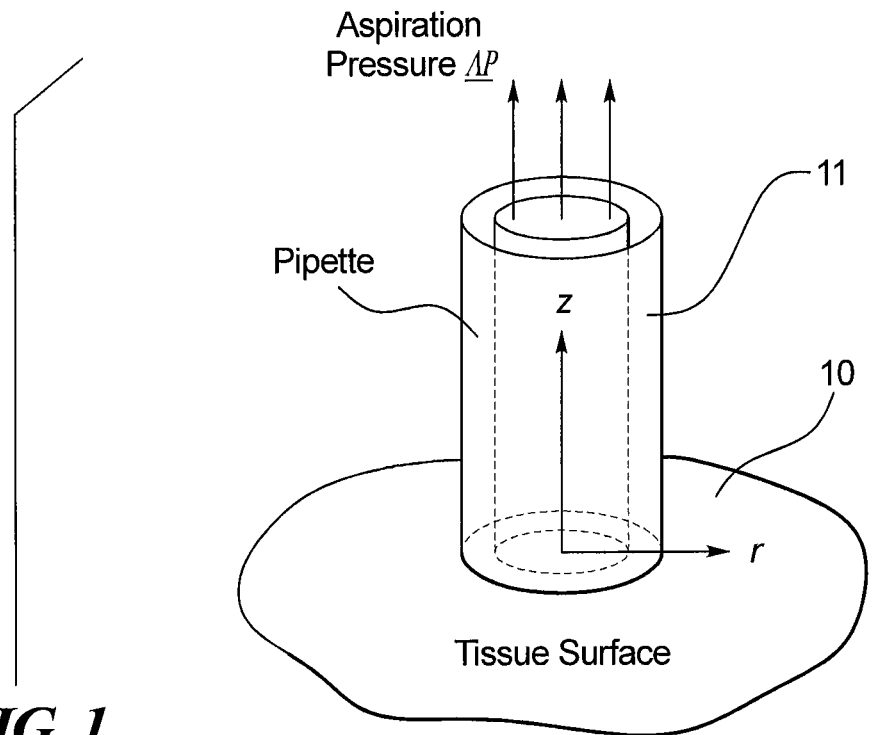
FIG. 1 is a schematic illustration of the underlying principal of the disclosed device and method.
Figure 1:
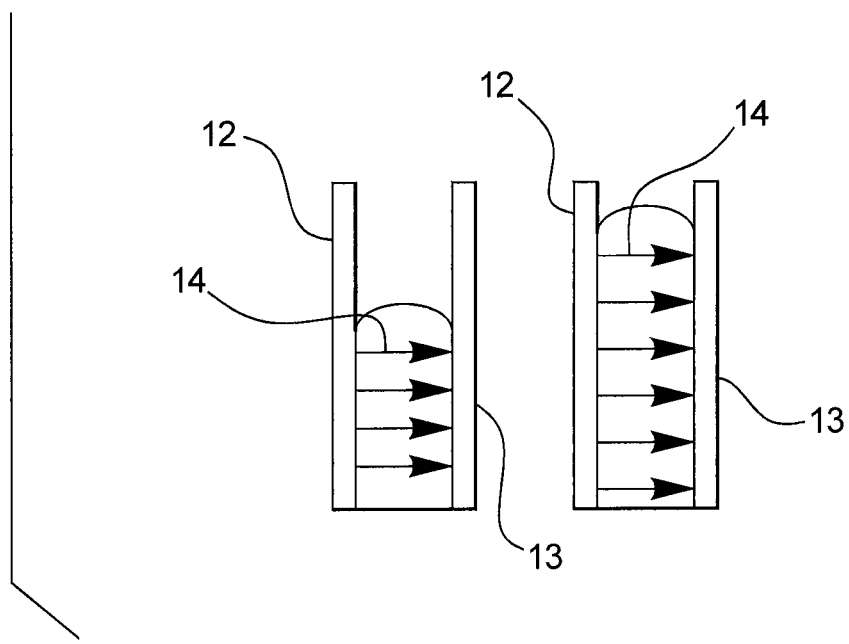

This disclosure is generally related to a device for evaluation of a tissue's biological or biomechanical character with its operation principal illustrated in FIG. 1. The tested tissue 10 is drawn into an aspiration tube 11 under negative pressure and the elongation or deformation of the tissue is measured by a change in one or more parameters associated with the electric or magnetic field defined by two opposing electrodes (12, 13) disposed within the aspiration tube 11.

For example, when current is sent through the pair of electrodes (12, 13), directional vectors 14 of the current occur along the electrodes, representing a total sum. This sum of current vectors has a direct relationship to the total resistance and voltage between the electrodes. Thus, as more or less paths become available for the current vectors 14 to travel from one electrode to another, the resistance and voltage of the electric or magnetic field between the two electrodes change. Specifically, as more conduction paths become available between the electrodes, the resistance decreases. On the contrary, as fewer paths become available for current travel, the resistance increases.

In addition to the resistance, changes in other parameters associated with the electric or magnetic field also occur. For example, the electrical fields have a direct relationship to the voltage between the electrodes. Measurement of the electric field in or around the aspiration tube may be dependent on the dielectric between the two electrodes. Therefore, elongation of the tested tissue across the electrodes may be reflected by a dielectric change in the electric field between the electrodes. Other suitable parameters that may be measured include, but are not limited to, voltage, magnetic dipole, inductance, capacitance, etc.

Figure 2:
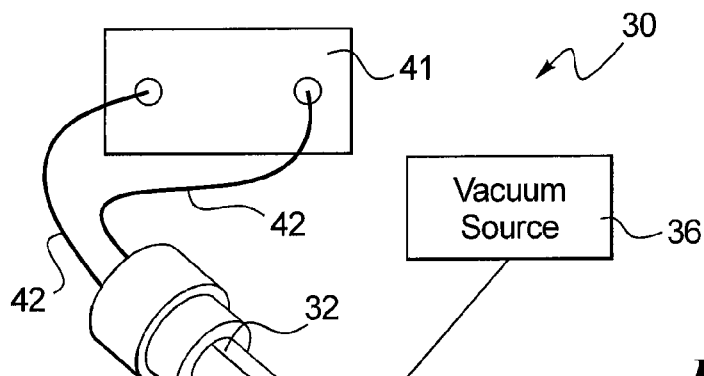
FIG. 2 is a side perspective view of one embodiment of the disclosed device.
Figure 3:
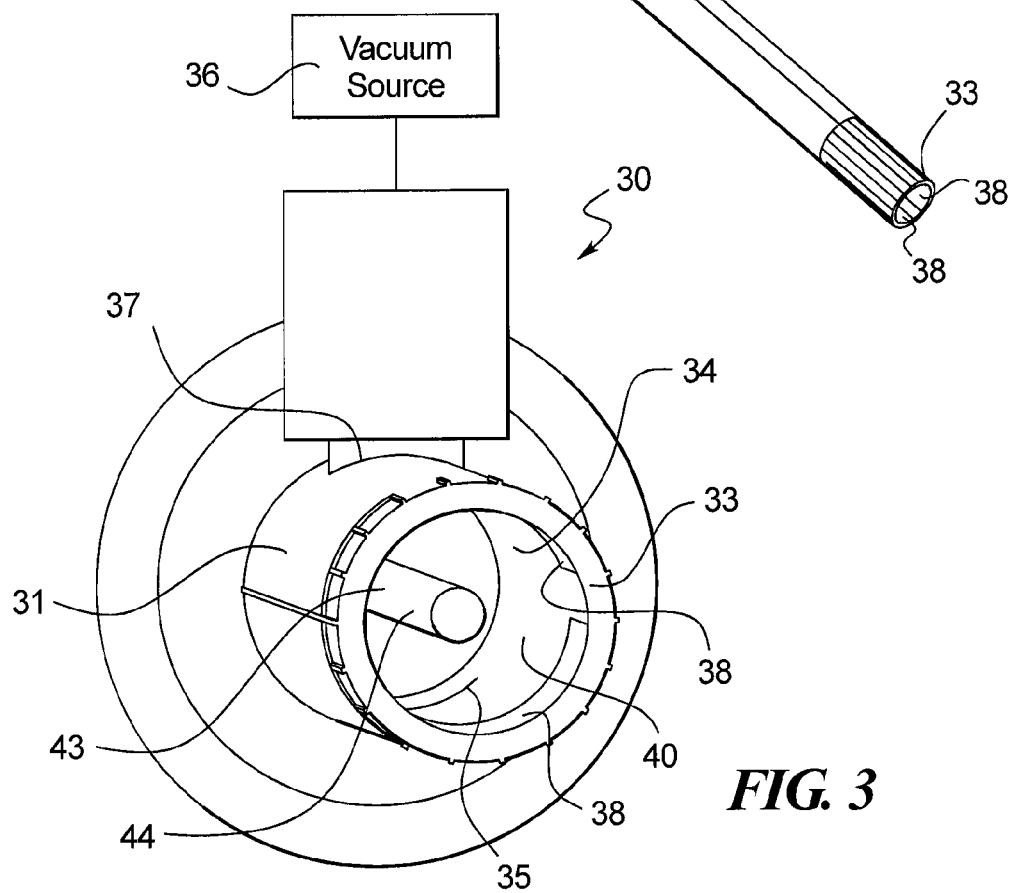
FIG. 3 is a bottom perspective view of the disclosed device shown in FIG. 2.

Turning to FIGS. 2-3, one embodiment of the disclosed device 30 includes a longitudinally extending sidewall 31 extending between proximal and distal ends (32, 33). The distal end 33 may be smooth in order to form a tight seal when the tested tissue is drawn into the device 30 without causing any tearing or ripping to the tissue or local hematoma. The sidewall 31 has an interior surface 34 that define an internal lumen 35. Although the internal lumen 35 is shown as straight and longitudinally uniform, it should not be construed as limiting the scope of this disclosure as the lumen may be curved and/or longitudinally non-uniform in other embodiments. Moreover, while the cross-sectional profile of the internal lumen 35 is shown as circular in FIGS. 2-3, other shapes such as oval, square, triangular, or even irregularly-shaped cross-sections may also be used by one of ordinary skill in the art in view of this disclosure.

As illustrated in FIG. 3, the internal lumen 35 is adapted to be operatively connected to a vacuum source 36. In one embodiment, the vacuum source is a suction pump, such as a syringe pump, that provides partial vacuum. However, it is to be understood that the type and capacity of the vacuum source should not be considered as limiting the scope of this disclosure. For example, the vacuum source may simply be a central vacuum system used in most medical and/or research facilities. Moreover, the applied negative pressure may be held constant throughout the evaluation or it may be varied or program to further enhance tissue differentiation.

In FIGS. 2-3, the internal lumen is connected to the vacuum source 36 through an aspiration port 37 provided on the sidewall 31 in the vicinity of the proximal end 32. However, this configuration is not meant to limit the scope of this disclosure. The vacuum source 36 may be connected to the internal lumen 35 through the proximal end 32 or other suitable location of the sidewall 31 in view of this disclosure.

In order to detect and/or measure the elongation of the tested tissue within the internal lumen 35, the device 30 includes a distal electrode pair 38 disposed within the internal lumen 35. The distal electrode pair 38 may be secured to the interior surface 34 of the sidewall 31. As shown in FIG. 3, the distal electrode pair 38 may be positioned directly opposing each other. The distal electrode pair 38 may be made from a sheet of metal or metal alloy typically used as electrode materials. The dimensions of the electrodes are based on the dimension of the sidewall 31, such as its length and cross-sectional area, and should be apparent to one of ordinary skill in the art in view of this disclosure. In one embodiment, the distal electrode pair 38 is adhesively secured to the sidewall 31. However, other securing mechanisms, such as welding, smelting, or through a printable circuit board, may also be used without undue experimentation. Moreover, at the end of the evaluation the aspiration port 37 may also be disconnected from the vacuum source 36 and connected to a reconditioning system (not shown) to clean the internal lumen 35 (e.g. by flushing a cleaning solution therethrough) and/or to re-sensitizing the electrodes. Alternatively, the reconditioning system may be connected to the internal lumen through a separate port thereby allowing the device to be cleaned and re-sensitized while negative pressure is still applied.

As discussed earlier, the distal electrode pair 38 defines an electric or magnetic field 40 that is subject to change as the tested tissue is elongated across the electrodes. In order to detect or measure such changes, the device 30 further includes a detector 41 operatively connected to the distal electrode pair 38, such as through a pair of insulated wires 42 to detect at least one parameter associated with the electric or magnetic field 40. In one embodiment, the parameter is the resistance between the distal electrode pair 38. In another embodiment, the parameter is the voltage between the distal electrode pair 38.

To further improve its evaluation performance, the device 30 further includes an optional indenter 43 adapted to apply a positive stress on the tested tissue and evaluate its response to such a pressure. As illustrated in FIG. 3, the indenter 43 includes a probe 44 adapted to apply a positive stress on the tested tissue within the internal lumen 35. In one embodiment, the probe 44 is extendable in a distal direction within the internal lumen 35. In another embodiment, the probe 44 may be in a fixed position and the positive stress is applied as the tested tissue elongates beyond the point of contact with the tip of the probe 44. The probe 44 is connected to a sensor 45 (not shown) that measures the position of the probe, the force or pressure exerted on the tested tissue by the probe, or other suitable parameters. Because the tested tissue is already secured to the evaluation device 30, the ability of the indenter 43 to accurately measure the response of the tested tissue may be synergistically improved. Moreover, the measurements obtained by the indenter 43 can be combined with the one or more parameters associated with the electric or magnetic field 40 to further enhance the evaluation performance of the disclosed device 30.

In addition to the negative pressure and optional positive stress, electric and/or magnetic stimulation may also be applied on the tissue, such as through the distal electrode pair. The electric and/or magnetic stimulation may be constant, pulsed, or programmed in terms of intensity and timing. The tissue's response to such stimulation may then be evaluated by the disclosed device, either independently or in combination with the tissue's response to other stimulations disclosed herein. In some embodiments, it may be desirable to have only one electrode of the distal electrode pair activated to measure and/or stimulate the target tissue while in other embodiments activation of both electrodes are required.

A non-limiting example of the device 30 is provided as follows. An aspiration tube made of Pyrex 7740 Borosilicate Glass Tubing (10.6 mm diameter) is fitted with a silicone tubing at its proximal end. Two electrodes made from a sheet of Beryllium Copper C172 (0.15 mm thick) were cut to the dimensions of 15×7 mm. The two plates were soldered to insulated wiring, mounted directly across from each other inside the distal end of the aspiration tube by applying Loctite® Stick'N Seal glue, and allowed to set overnight. The insulated wires were extended through the silicon tubing and connected to a Validyne USB2250 data acquisition system, which in turn is interfaced with a standard PC through a Validyne software to measure the resistance between the two electrodes. The suction pressure was created by using a 60 ml syringe coupled with a WPI Aladdin-6000 pump connected to the silicon tubing. A Validyne pressure transducer is connected with the syringe pump and the data acquisition system. In this non-limiting example, the optional indenter is not included.

The above-described exemplary device was used to test several samples of different porcine tissues. Specifically, freshly excised porcine organs (heart, kidney, liver, and lung) were collected at a local slaughterhouse in bio-safety bags. Each sample was mounted on a Petri dish, and the tip of the aspiration tube was firmly pressed against the tissue sample before suction pressure was applied. The aspiration tube was mounted and held at an angle to ensure a leak-free contact. Six repetitions were performed on each sample at a centralized spot. It is to be understood that the disclosed device and method may be used to evaluate a wide variety of tissues by one of ordinary skill in the art and are therefore not limited to the four tissues used in the demonstrative experiment disclosed herein.

Figure 4:
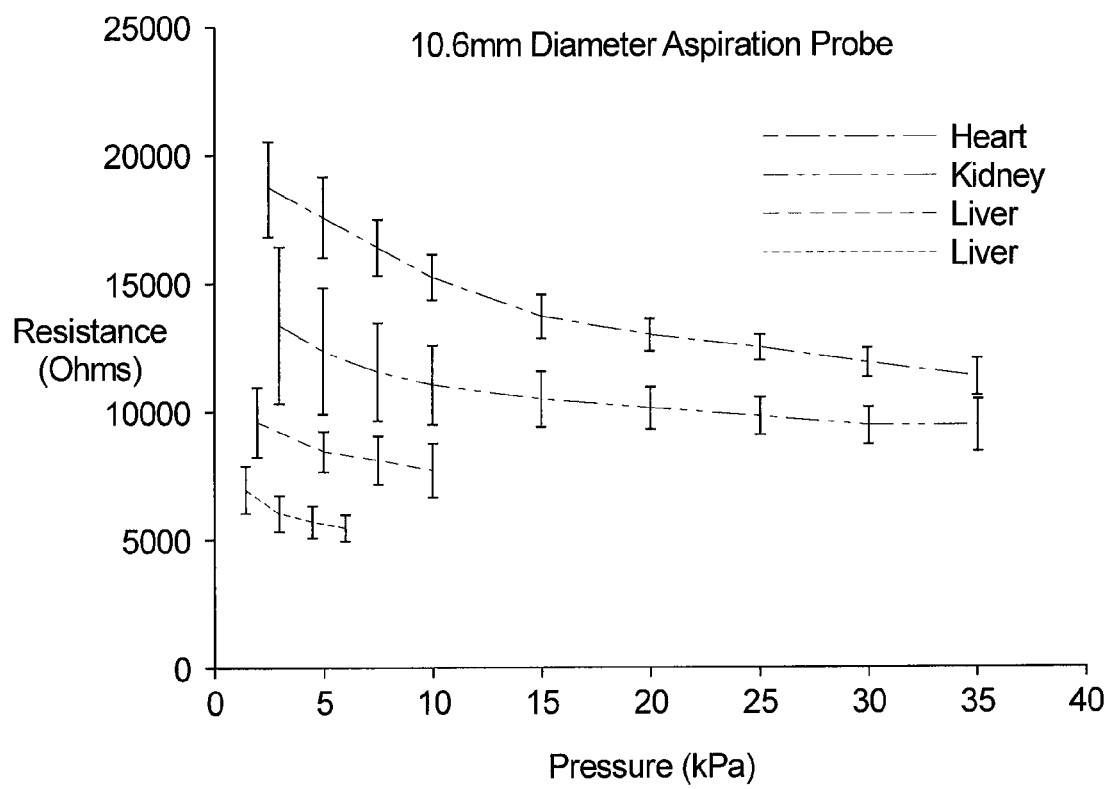
FIG. 4 is a graphic illustration of the relationship between the resistance and the negative pressure applied to the tested tissue in the embodiment shown in FIGS. 2-3.
Figure 5:
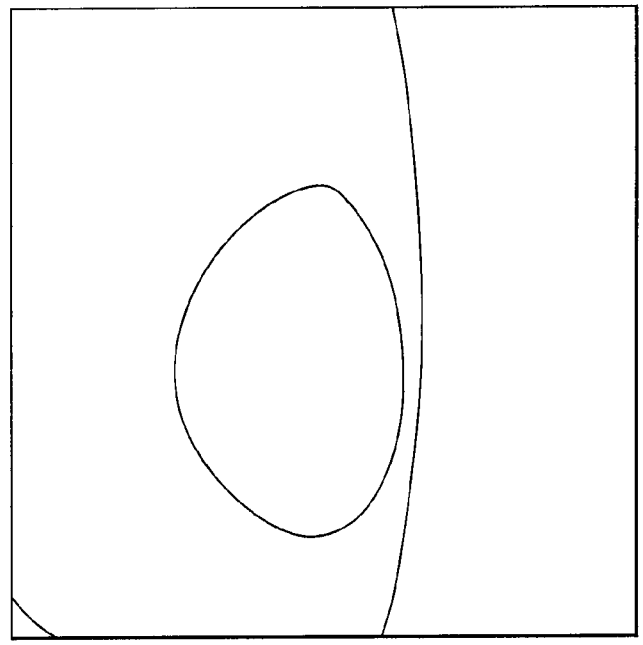
FIG. 5 is a photographic illustration of the minimally invasive nature of the disclosed device.

As illustrated in FIG. 4, a tight dispersion of standard deviations (approximately 10% of the average value) was observed for each tested sample, which indicates repeatability of the device to produce similar results within a similar area of the organ. The heart, the stiffest of all of the tissue samples, showed the highest overall resistance values. The most compliant of the tissue samples, the lung, produced the lowest average resistance values. Moreover, as illustrated in FIG. 5, a kidney sample showed no tearing or ripping after the test is completed, which demonstrates the minimally invasive natural of the disclosed device. The test showed the ability of the device to differentiate different tissue samples based on their biomechanical reaction toward the negative pressure.

In all cases, a nonlinear relation between the suction pressure and resistance was observed. At lower pressures, the resistance dropped sharply as the tested tissue elongates relatively rapidly through the electrodes, while saturating to a constant level was observed at higher pressures. A nonlinear response was expected as tissue elongates over a pair of electrodes, which can be inferred from the exponential equation for resistance of a material between two points: $R=\rho*L/A$, where R is resistance, $\rho$ is resistivity, L is length, and A is area. Here, the resistivity and length (distance between electrodes) are constant; the only variable is the cross sectional area. As tissue extends over an electrode pair, the cross-sectional area increases, causing an exponential decrease in resistance R.

Turning now to FIGS. 6-9, the disclosed device 30 may further include, in addition to the distal electrode pair 38, at least one proximal electrode pair 50 disposed within the internal lumen 35 and operatively connected to the detector 41, such as through one or more pairs of insulated wires 51. Like the distal electrode pair 38, the at least one proximal electrode pair 50 are also secured to the interior surface 34 of the sidewall 31 proximal to the distal electrode pair 38. In the non-limiting embodiment illustrated in FIGS. 6-9, the proximal and distal electrode pairs are incorporated into a printable circuit board (PCB) 53, which is securely fitted to the interior surface 34 of the sidewall, with or without the use of adhesives. Although five proximal electrode pairs are shown in FIGS. 6-9, it is to be understood that the number of the proximal electrode pair(s) may also be 1-4 or greater than 5.

Figure 6:
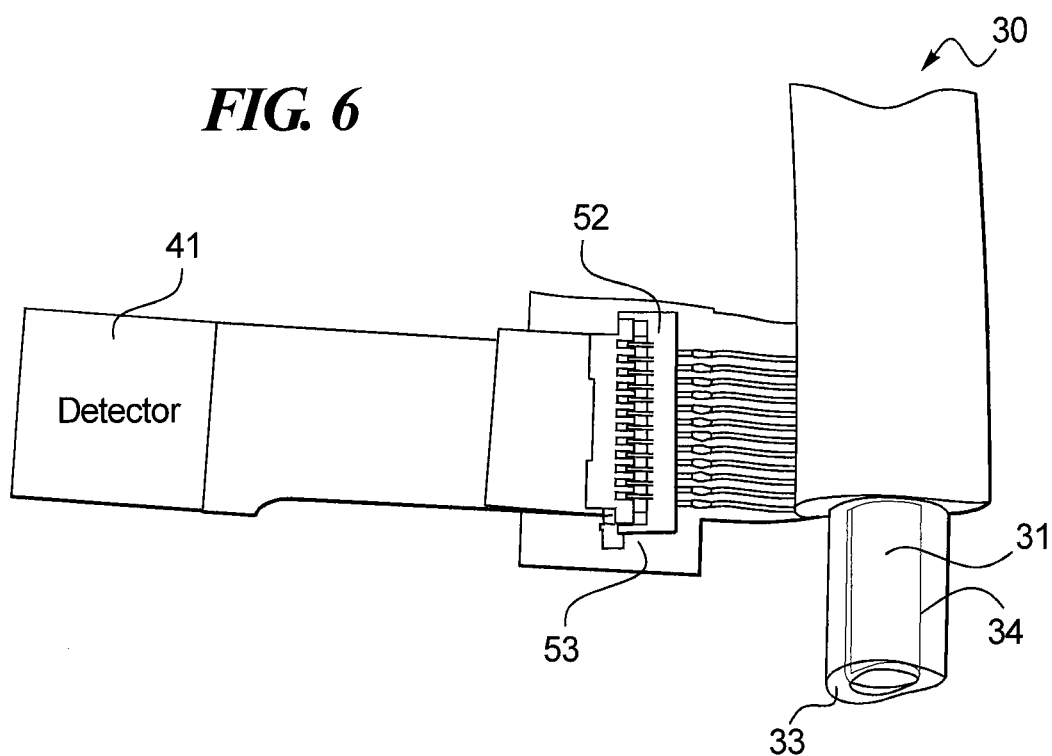
FIG. 6 is a photographic illustration of another embodiment of the disclosed device.
Figure 7:
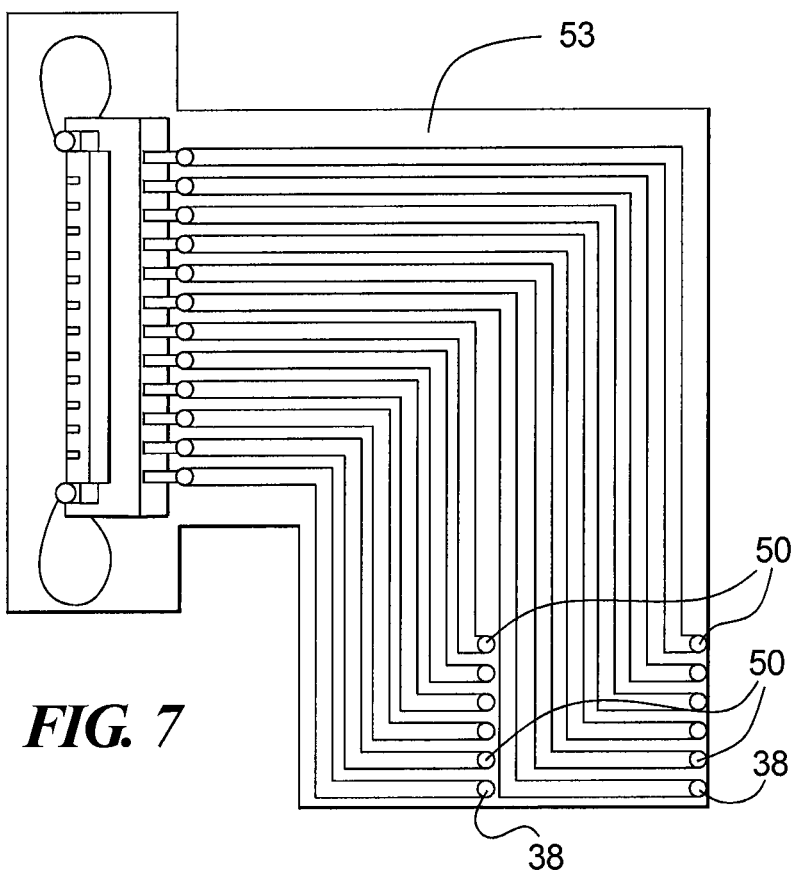
FIG. 7 is a photographic illustration of a printable circuit board used in the device shown in FIG. 6.
Figure 8:
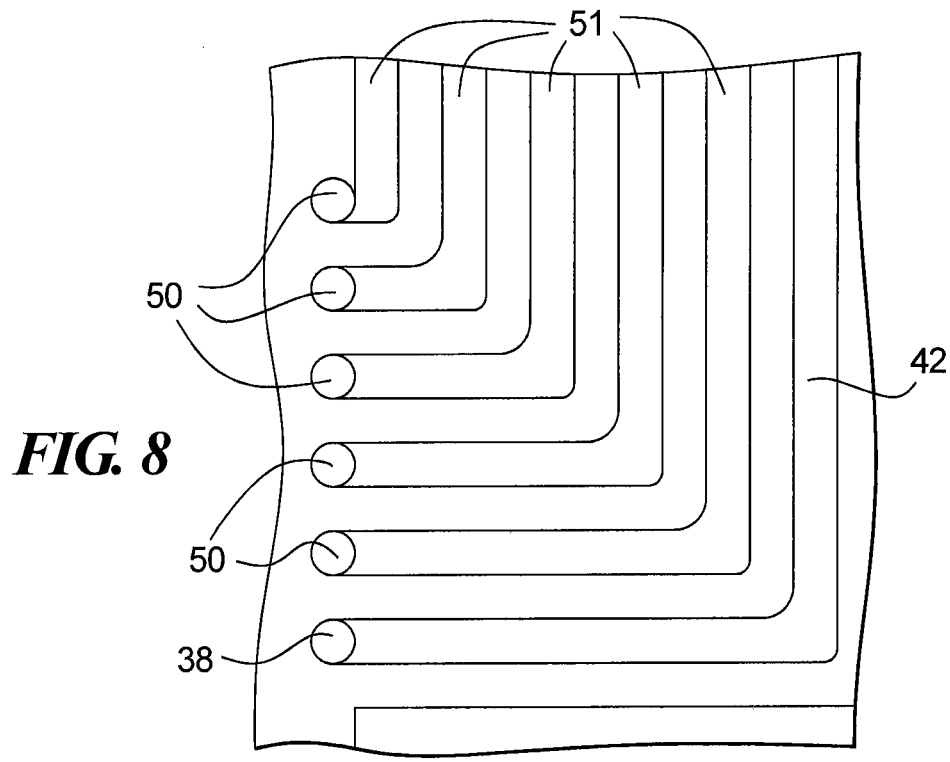
FIG. 8 is an photographic illustration of the printable circuit board in FIG. 7, particularly showing the in-line arrangement of the electrodes.
Figure 9:
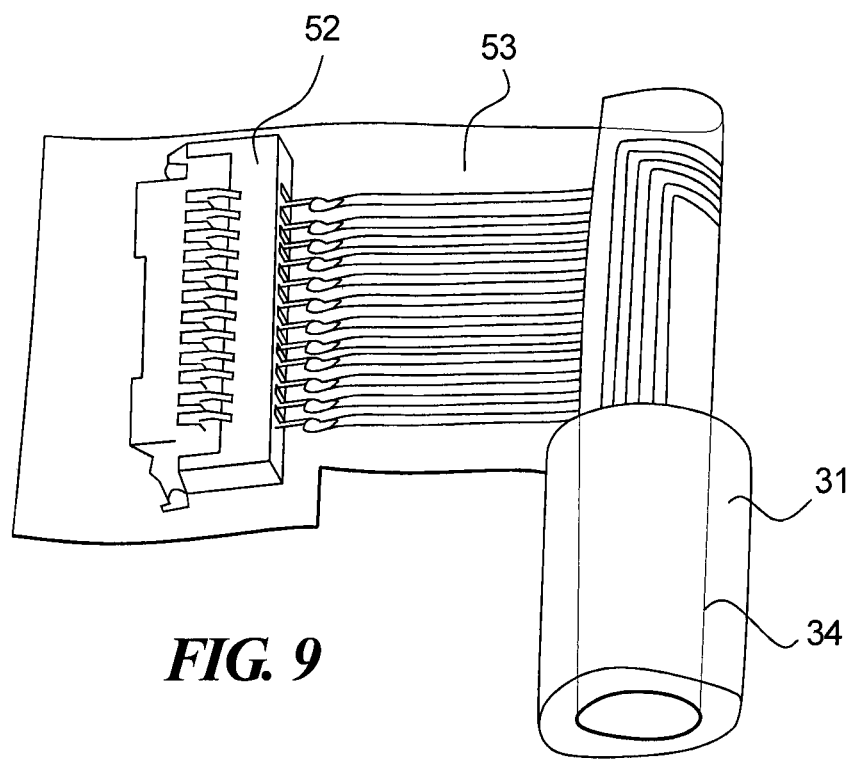
FIG. 9 is a partial view of the device shown in FIG. 6, particularly illustrating the printable circuit board inserted into the sidewall of the device.

Again, each proximal electrode pair 50 may include two electrodes positioned directly opposite to each other. Moreover, the proximal and distal electrode pairs (50, 38) may form a longitudinally in-line array of electrode pairs, as particularly illustrated in FIGS. 7 and 8. In one embodiment, the array of electrode pairs is longitudinally equidistant. Further, as illustrated in FIG. 6, the electrode pairs (50, 38) may be connected to the detector 41 through a multiple-pin micro-connector 52.

Similar to the single electrode pair embodiment discussed earlier, the multi-electrode pair device 30 illustrated in FIGS. 6-9 may also include an optional indenter 43 adapted to apply a positive stress on the tested tissue and measure its response toward such a pressure stimulation in order to further enhance the evaluation performance of the device 30. Moreover, although the distal and proximal electrode pairs (38, 50) are shown in FIGS. 2-3 and 6-9 as being secured to the sidewall 31, it is to be understood that each electrode pair may be secured to the optional indenter 43, or may have one electrode secured to the sidewall 31 and the other electrode secured to the indenter 43.

Again, besides the negative pressure and optional positive stress, electric and/or magnetic stimulation may also be applied on the tissue, such as through the distal and/or proximal electrode pairs. The electric and/or magnetic stimulation may be constant, pulsed, or programmed in terms of intensity and timing. The tissue's response to such stimulation may then be evaluated by the disclosed device, either independently or in combination with the tissue's response to other stimulations disclosed herein. In some embodiments, it may be desirable to have only one electrode of the electrode pair (distal or proximal) activated to measure and/or stimulate the target tissue while in other embodiments activation of both electrodes are required.

A non-limiting example of the multi-electrode pair device 30 is provided as follows. Six pairs of gold plated electrodes were printed on flexible printable circuit board. The electrodes were 200×200 um in size, and arranged in a linear stack, with each electrode 200 um away from the adjacent electrode(s). The electrodes were attached to fabricated wires on the board that were approximately the same width of 200 um; the fabricated wires were connected to a 12-pin micro-FFC connector for external hookup. The circuit board was coated with an insulated layer so that only the electrodes were exposed and responsive. When rolled into the shape of a cylinder, the two rows of electrodes were aligned directly across from each other, and the entire circuit board could fit into the tip of a 2.4 mm diameter Pyrex aspiration tube.

Once the circuit board with electrodes was fitted into the distal end of the aspiration tube, the proximal end of the aspiration tube is fitted with a silicon tube. The micro-connector protruded from the side, and silicon glue was used to close any gaps and create a vacuum seal for applying suction. The opposite end of the silicon tubing was connected to a syringe pump in a similar way as the single electrode-pair example. The 12-pin micro-connector was connected to the Validyne system.

The multi-electrode pair exemplary device described above is used to test a hydrogel sample to demonstrate the device's ability to provide spatial differentiation to the elongation of the sample within the aspiration tube. The hydrogel may be an agarose gel prepared as follows: a mixture of agarose powder and D.I. water (1:100 by weight) was heated until boiling and subsequently cooled to room temperature to form a gel. The tests were performed within an hour of cooling to ensure no dehydration of the gel occurred.

As illustrated in FIG. 10, the multi-electrode pair device was very effective in precisely identifying when tissue had crossed an electrode pair. During the period when no tissue was currently between a pair of electrodes, the resistance measurements would be extremely large, since the connection was an open circuit, which has a theoretically infinite resistance. As tissue hit an electrode pair, the nonlinear (exponential) change in resistance is observed, and an order of magnitude drop in resistance occurs in a very short time, as illustrated in the almost vertical lines in FIG. 10. This sharp drop in resistance represents the exact pressure at which tissue hits an electrode pair. Four sharp drops in resistance were observed in FIG. 10, indicating that the four electrode pairs were crossed by the elongated sample.

The device may be used alone or in combination with other medical devices, such as by coupling with a catheter, an endoscopy or a tracheal tube. The device may also include other functions besides evaluation of a tissue's biological or biomechanical character. In one particular embodiment, the device may further include a cutter (not shown) disposed at or close to the distal end of the sidewall to excise the tissue (or portion thereof) that is drawn into the device under the negative pressure. In one refinement, excision is performed when tissue evaluation indicates abnormality. The excised tissue (still in the device) is then withdrawn from the body with the device for further in vitro tests.

In another embodiment, an optical fiber or other visualization implement is included in the device to enable visualization, such as through intrinsic fluorescence, of cellular or tissue behavior as the tissue is measured and/or stimulated by the electrode pairs and/or the indenter, thereby further enhancing the evaluation performance of the device. The optical fiber or other visualization implement may be disposed within the lumen or along the exterior surface of the sidewall so that the device substantially maintains its low profile. Moreover, the optical fiber or visualization implement may be guided to navigate through or around the tested tissue (within or outside of the device) to enhance sensitivity of tissue evaluation.

According to another aspect of this disclosure, a method for evaluating biomechanics of a target tissue is disclosed. As illustrated in FIG. 11, the disclosed method (100) includes the steps of: providing a evaluation device comprising a longitudinally extending sidewall terminating into an open distal end and having an interior surface defining an internal lumen, and a distal electrode pair secured to the interior surface of the sidewall, the electrodes defining an electric or magnetic field therebetween (101); contacting the target tissue with the distal end of the sidewall (102); drawing a portion of the target tissue into the evaluation device through the distal end and in contact with the distal electrode pair by connecting the internal lumen to a vacuum source (103); and measuring at least one parameter associated with the electric or magnetic field (104). In one embodiment, the parameter is the resistance between the distal electrode pair.

In another embodiment, the disclosed method (100) may further include the optional step of distally applying a positive stress on the target tissue (105). The application of positive stress may occur before, while, or after the measurement of the parameter.

In a refinement, in which the evaluation device further comprises at least one proximal electrode pair operatively connected to the detector, wherein the at least one proximal electrode pair is secured to the interior surface of sidewall proximal to the distal electrode pair, the disclosed method (100) may also include the optional steps of: allowing the target tissue to be drawn into the evaluation device and in contact with the proximal electrodes (106) and measuring at least one parameter associated with the electric or magnetic field defined by each proximal electrode pair (107).

INDUSTRIAL APPLICABILITY

The evaluation device disclosed herein may have a wide range of medical applications, such as for minimally invasive and/or in vivo analysis of target tissues. However, the device may also be used in vitro (e.g. on tissues excised through biopsy) or used in some evaluations that result in tissue tearing or ripping. Although soft tissues are used as examples to demonstrate the performance of the disclosed device, harder tissues, such as bones, may also be analyzed by the disclosed device. Moreover, the device or part of the device may be made disposable for a wider range of medical applications.

The device may be miniaturized or scaled-up from embodiments disclosed herein, depending on its application. Moreover, a plurality of the disclosed device may be used to simultaneously evaluation different tissues or different areas of one tissue. Finally, the disclosed device may be used as in electrical impedance tomography (EIT), which is a medical imaging technique in which an image of the conductivity or permittivity of part of the body is inferred from surface electrical measurements. For example, small alternating currents may be applied to some or all of the electrode pair of the device and the resulting electrical potentials are measured and/or mapped over time to generate an "image" of the tested tissue. In addition, the disclosed device or method may be used with inverse modeling (computational finite-element) to identify features deep in the tissue based on the responses in different loading configurations. For example, a stiff tumor located 1 cm deep will influence the biomechanics of the tissue at the surface via its attachment to the outer layers.

While only certain embodiments have been set forth, alternative embodiments and various modifications will be apparent from the above descriptions to those skilled in the art. These and other alternatives are considered equivalents and within the spirit and scope of this disclosure.

What is claimed is:

1. A tissue evaluation device for evaluating a tissue's mechanical properties, said device comprising:
    an elongated tube extending between proximal and distal ends, said tube having an interior wall defining a longitudinally extending lumen, wherein the distal end of the tube has an opening leading to the lumen;
    a plurality of electrode pairs disposed within the lumen and secured to an interior surface of the interior wall, each pair of electrodes spaced apart along at least a portion of a length of the tube at different longitudinal positions starting from the opening at the distal end of the tube, wherein at a given longitudinal position electrodes of each pair are spaced apart with respect to the lumen, and wherein the electrodes of each electrode pair are configured to create an electric or magnetic field therebetween;
    a vacuum source operatively coupled to the lumen near the proximal end of the tube and configured to apply varying pressures to the lumen of the device; and
    a detector comprising a data acquisition system operatively connected to the plurality of electrode pairs and the vacuum source, the detector being configured to detect one or more parameters selected from resistance, impedance, voltage, inductance, capacitance, and combinations thereof, and to determine the tissue mechanical properties from the one or more parameters detected as the tissue elongates in the lumen.

2. The device of claim 1, wherein a cross-sectional profile of the lumen is circular, elliptical, triangular, square, or irregular.

3. The device of claim 1, wherein electrodes of each electrode pair are spaced directly opposite each other at their given longitudinal position.

4. The device of claim 1, wherein the vacuum source comprises a suction pump.

5. The device of claim 4, wherein the electrodes of the plurality of electrode pairs are each made of beryllium copper.

6. The device of claim 5, wherein each of the plurality of electrode pairs is adhesively secured to the interior surface of the tube wall.

7. The device of claim 1, wherein the detector is connected to each of the plurality of electrode pairs through a pair of insulated wires.

8. The device of claim 1, wherein the at least one parameter is resistance.

9. The device of claim 1, wherein the plurality of electrode pairs are connected to the detector through a multiple-pin micro-connector.

10. The device of claim 1, further comprising an indenter positioned inside the lumen near the distal end of the tube.

11. A method for evaluating mechanical properties of a target tissue, said method comprising:
provide the evaluation device of claim 1;
contacting the opening at the distal end of the tube of the device to the target tissue;
applying, from the vacuum source, a negative pressure to the lumen of the device causing at least a portion of the target tissue to elongate through the opening into the lumen and across at least a first electrode pair of the plurality of electrode pairs;
detecting, with the detector, one or more parameters from one or more of the plurality of electrode pairs; repeating said applying and detecting, wherein the negative pressure applied is varied with each repetition and the target tissue increasingly elongates proximally through the lumen; and
evaluating, with the detector, the mechanical properties of the tissue.

12. The method of claim 11, wherein the one or more parameters detected is resistance.

13. The method of claim 11, wherein said detecting involves detecting at least two parameters from one or more of the plurality of electrode pairs.

14. The method of claim 11, wherein the device further comprises an indenter positioned inside the lumen near the distal end of the tube, said method further comprising:
contacting the target tissue that has elongated into the lumen with the indenter, and measuring a response of the target tissue to said contacting, wherein said evaluating is based on said detecting and said measuring.

15. The method of claim 11, wherein one or more electrode pairs of the plurality of electrode pairs is configured to apply electric or magnetic stimulation, said method further comprising:
stimulating target tissue that has elongated into the lumen and is positioned between one or more of the plurality of electrode pairs, and
measuring a response of the target tissue to said stimulating, wherein said evaluating is based on said detecting and said measuring.

16. A method for evaluating mechanical properties of a target tissue, said method comprising:
providing a tissue evaluation device, said device comprising:
an elongated tube extending between proximal and distal ends, said tube having an interior wall defining a longitudinally extending lumen, wherein the distal end of the tube has an opening leading to the lumen;
at least one electrode pair disposed within the lumen and secured to the interior surface of the tube wall near the distal end of the tube, wherein electrodes of the electrode pair are spaced apart with respect to the lumen, and wherein the electrodes of the electrode pair are configured to create an electric or magnetic field between them;
a pressure source operatively coupled to the lumen near the proximal end of the tube and configured to apply pressure to the lumen of the device; and
a detector comprising a data acquisition system operatively connected to the pressure source and the at least one electrode pair, the detector being configured to detect one or more parameters selected from resistance, impedance, voltage, inductance, capacitance, and combinations thereof and to determine the tissue mechanical properties from the one or more parameters detected as the tissue elongates in the lumen;
contacting the opening at the distal end of the tube of the device with the target tissue;
applying, from the pressure source, a negative pressure to the lumen of the device causing at least a portion of the target tissue to elongate through the opening into the lumen and across the at least one electrode pair;
detecting, with the detector, one or more parameters from the electrode pair;
repeating said applying and detecting, wherein the negative pressure applied is increased with each repetition and the target tissue increasingly elongates proximally through the lumen;
evaluating with the detector, the mechanical properties of the tissue.

17. The method of claim 16, wherein the one or more parameters detected is resistance.

18. The method of claim 16, wherein said detecting involves detecting at least two parameters from the at least one electrode pair.

19. The method of claim 16, wherein the device further comprises an indenter positioned inside the lumen near the distal end of the tube, said method further comprising:
contacting target tissue that has elongated into the lumen with the indenter, and
measuring a response of the target tissue to said contacting, wherein said evaluating is based on said detecting and said measuring.

20. The method of claim 16, wherein the at least one electrode pair is configured to apply electric or magnetic stimulation, said method further comprising:
stimulating target tissue that has elongated into the lumen and is positioned between the at least one electrode pair, and
measuring a response of the target tissue to said stimulating, wherein said evaluating is based on said detecting and said measuring.

21. A tissue evaluation device for evaluating mechanical properties of a tissue sample, said device comprising:
an elongated tube having a proximal end and a distal end, the tube having an interior wall defining a lumen extending longitudinally along the elongated tube to an opening defined at the distal end of the tube;
a plurality of electrode pairs disposed on the interior wall of the lumen, the plurality of electrode pairs comprising at least a first electrode pair disposed at a first longitudinal position of the interior wall adjacent the opening and a second electrode pair being inwardly spaced apart from the first electrode pair at a second longitudinal position of the interior wall, wherein the first electrode pair is configured to create an electric or magnetic field therebetween and wherein the second electrode pair is configured to create an electric or magnetic field therebetween;

wherein a first cross-section at the first longitudinal position of the interior wall is at least substantially the same as a second cross-section at the second longitudinal position of the interior wall; and a detector comprising a data acquisition system operatively connected to the plurality of electrode pairs, the detector being configured to detect one or more parameters selected from resistance, impedance, voltage, inductance, capacitance, and combinations thereof and to determine the tissue mechanical properties from the one or more parameters detected as the tissue elongates in the lumen.

22. The tissue evaluation device of claim 21, further comprising a vacuum source operatively coupled to the lumen to selectively apply a negative pressure to the lumen.

23. The tissue evaluation device of claim 21, wherein an angle between a line of force generated at the opening by a negative pressure is at least substantially perpendicular to the interior wall.

24. The tissue evaluation device of claim 21, wherein the first cross-section and the second cross-section are one of a circle, an oval, a square, a triangle, or an irregularly-shaped cross-section.

25. The tissue evaluation device of claim 22, wherein the plurality of electrode pairs further comprises a third electrode pair disposed inwardly and spaced apart from the second electrode pair at a third longitudinal position of the interior wall, wherein the third electrode pair is configured to create an electric or magnetic field therebetween, and wherein a third cross-section at the third longitudinal position of the interior wall is at least substantially the same as the first cross-section at the first longitudinal position of the interior wall and the second cross-section at the second longitudinal position of the interior wall.

* * * * *